United States Patent
Neuba et al.

(10) Patent No.: US 9,511,009 B2
(45) Date of Patent: *Dec. 6, 2016

(54) REDUCTION OF THE AUTOXIDATION OF AGENTS FOR THE OXIDATIVE DYEING AND/OR BLEACHING OF KERATIN FIBERS

(71) Applicant: Henkel AG & Co. KGaA, Duesseldorf (DE)

(72) Inventors: Constanze Neuba, Grevenbroich (DE); Frank Janssen, Cologne (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/737,909

(22) Filed: Jun. 12, 2015

(65) Prior Publication Data

US 2015/0272849 A1  Oct. 1, 2015

Related U.S. Application Data

(63) Continuation of application No. PCT/EP2013/076050, filed on Dec. 10, 2013.

(30) Foreign Application Priority Data

Dec. 14, 2012  (DE) .......... 10 2012 223 207

(51) Int. Cl.
| | |
|---|---|
| *A61Q 5/10* | (2006.01) |
| *A61K 8/60* | (2006.01) |
| *A61K 8/41* | (2006.01) |
| *A61K 8/34* | (2006.01) |
| *A61K 8/46* | (2006.01) |
| *A61Q 5/08* | (2006.01) |

(52) U.S. Cl.
CPC .............. *A61K 8/604* (2013.01); *A61K 8/347* (2013.01); *A61K 8/411* (2013.01); *A61K 8/415* (2013.01); *A61K 8/463* (2013.01); *A61Q 5/08* (2013.01); *A61Q 5/10* (2013.01); *A61K 2800/522* (2013.01)

(58) Field of Classification Search
CPC ........... A61Q 5/10; A61Q 5/08; A61K 8/415; A61K 8/604; A61K 8/347
USPC ............................................. 8/405
See application file for complete search history.

(56) References Cited

U.S. PATENT DOCUMENTS

| | | | |
|---|---|---|---|
| 3,488,138 A | 1/1970 | Iscowitz | |
| 4,875,902 A | 10/1989 | Grollier et al. | |
| 5,318,599 A * | 6/1994 | Lorenz ................. | A61K 8/4926 8/405 |
| 5,670,471 A * | 9/1997 | Amalric ................. | A61K 8/342 424/70.31 |
| 5,716,418 A | 2/1998 | Matzik et al. | |
| 8,845,759 B2 * | 9/2014 | Neuba ..................... | A61K 8/498 8/405 |
| 2009/0246160 A1 | 10/2009 | Simonet et al. | |

FOREIGN PATENT DOCUMENTS

| | | |
|---|---|---|
| DE | 102005005199 A1 | 8/2006 |
| DE | 102007027862 A1 | 12/2008 |
| JP | 2005-179191 A | 7/2005 |
| JP | 2011-37750 A | 2/2011 |
| KR | 10-2009-0027985 A | 3/2009 |
| WO | 2004/000248 A2 | 12/2003 |
| WO | 2012/095394 A2 | 7/2012 |

OTHER PUBLICATIONS

PCT International Search Report (PCT/EP2013/076050) dated Jan. 4, 2014.
Database GNPD [Online] Mintel, "Hair Sunscreen Colour Protect Cream", XP002722453, Database Accession No. 1398195, Sep. 2010.

* cited by examiner

*Primary Examiner* — Eisa Elhilo
(74) *Attorney, Agent, or Firm* — David K. Benson

(57) ABSTRACT

An agent for the oxidative dyeing of keratin fibers, in particular human hair, includes in a cosmetic carrier (a) at least one first alkyl glucoside of formula (I) set forth herein, in which R1 is an unbranched or branched, saturated or unsaturated $C_{20}$-$C_{28}$ alkyl group and n is an integer from 1 to 10, (b) at least one second alkyl glucoside of formula (II) set forth herein, in which R2 is an unbranched or branched, saturated or unsaturated $C_8$-$C_{18}$ alkyl group and m is an integer from 1 to 10, (c) at least one oxidation dye precursor of the developer type, and d) at least one oxidation dye precursor of the coupler type.

13 Claims, No Drawings

REDUCTION OF THE AUTOXIDATION OF AGENTS FOR THE OXIDATIVE DYEING AND/OR BLEACHING OF KERATIN FIBERS

FIELD OF THE INVENTION

The present invention generally relates to agents for dyeing and/or lightening of keratinic fibers, in particular human hair, which include in a cosmetic carrier a specific combination of two different alkyl glucosides having different alkyl chain lengths, an oxidation dye precursor of the developer type, and an oxidation dye precursor of the coupler type. The use of this specific combination for preventing the discoloration in oxidative agents for dyeing and/or lightening the keratin fibers, caused by atmospheric oxygen, is likewise the subject matter of the invention.

BACKGROUND OF THE INVENTION

Those skilled in the art of hair coloration are familiar with various coloring systems or color-changing cosmetic agents, which are selected depending on the requirement for the coloration. For long-lasting, intense colorations having appropriate fastness properties, so-called oxidation dyes are used. Such coloring agents customarily include oxidation dye precursors, so-called developer components and coupler components, which form the actual dyes with one another under the influence of oxidizing agents such as hydrogen peroxide. The oxidation dyes are characterized by excellent, long-lasting color results. In addition to the coloration, lightening or blond shading of the inherent hair color is specifically desired by many consumers. For this purpose, the natural or synthetic dyes which color the fiber are decolorized, usually oxidatively, using appropriate oxidizing agents such as hydrogen peroxide.

Oxidative coloring agents are customarily offered in the form of a kit (multi-component packaging unit) made up of two components, the first component including the oxidation dye precursors and an alkalizing agent (ammonia, for example), and the second component including the oxidizing agent. Peroxides, for example hydrogen peroxide, are generally used as the oxidizing agent. The kit also often includes a conditioner as a third component, which is applied after the actual dyeing operation to improve the care condition of the hair.

The oxidation dye precursors (developer and coupler) themselves are not colored; rather, the formation of the actual dyes takes place only in the course of application by contact of the oxidation dye precursors with the oxidizing agent (hydrogen peroxide). In a chemical reaction, the developers (such as p-phenylenediamine derivatives or p-aminophenol derivatives, for example) used as oxidation dye precursors are initially oxidatively converted, using hydrogen peroxide, into a reactive intermediate stage, also referred to as quinoneimine or quinonediimine, which then reacts with the couplers in an oxidative coupling reaction to form the particular dye.

Since the developers and couplers are initially oxidatively converted into reactive intermediate stages, and subsequently into dyes, by their nature they are highly sensitive to oxidizing agents.

The key factor to success for oxidative keratin dyeing is that the formation of the dyes takes place in a targeted manner using hydrogen peroxide, and does not occur within the keratinic fiber until during the dyeing operation. A premature reaction of developers with couplers results in premature dye formation, so that the dye precursors for the actual coloration within the keratin fibers are no longer available, or are no longer available in a sufficient quantity. To avoid this premature reaction of developers and couplers, the oxidation dye precursors are therefore customarily packaged separately from the oxidizing agent in various cosmetic carriers.

A problem which has been known for quite some time in the practice of hair dyeing is that not only is the formation of the dyes initiated by the targeted addition of oxidizing agent, but in addition, the atmospheric oxygen contained in the air acts as an oxidizing agent with respect to developers and couplers.

If a color cream that includes developers, couplers, and generally also alkalizing agents comes into contact with atmospheric oxygen, the dye formation is already initiated by the atmospheric oxygen before the actual dyeing operation begins. This undesirable process is also referred to as autoxidation of the dye precursors. Due to different reaction kinetics, in many cases the autoxidation of the oxidation dye products caused by atmospheric oxygen also does not result in the desired dyes, but instead, other nonspecific, less brilliantly colored and therefore undesirable reaction products are formed.

One consequence of the autoxidation is a cosmetically unsatisfactory, premature discoloration of the color cream, which is perceived by the user as extremely unattractive. Another consequence of the above-described autoxidation is a decrease in the coloring power of the corresponding coloring agent, since a not insignificant portion of the dye precursors prematurely reacts due to the atmospheric oxygen, and thus is no longer available for the actual dyeing operation.

A well-known method in the literature for minimizing the autoxidation of oxidation dye precursors is the use of reducing agents in the color creams. Examples of common suitable reducing agents are sodium sulfite or other alkali or alkaline earth sulfites, Vitamin C (ascorbic acid), and dehydroascorbic acid. In addition, thiol compounds such as cysteine, thioglycolic acid, or thiolactic acid may be used for minimizing the autoxidation in color creams, but they are less desirable due to the odor problems associated with this substance class.

Thus, in DE 10 2007 027862 A1, for example, a solution that includes a reducing agent is applied to already bottled hair coloring agents.

However, the use of reducing agents in color creams may also have disadvantages: like the oxidation dye precursors, the reducing agents also react with the oxidizing agent (hydrogen peroxide) during application. Accordingly, oxidizing agent which reacts with the reducing agents may no longer be available for the hair dyeing process as actually desired. In addition, the use of large quantities of reducing agent may thus result in a weakening of the coloring power of the coloring agent.

An optimal method for preferably completely preventing the autoxidation of oxidation dye precursors without having to rely on the use of large quantities of reducing agent is thus far not known from the prior art.

It is therefore desirable to provide agents for oxidative dyeing and/or lightening of hair which do not discolor, or which preferably discolor very little, due to contact with atmospheric oxygen. In addition, the ready-to-apply coloring agents which result after mixing with the oxidizing agent should not discolor, or preferably should discolor very little, due to contact with atmospheric oxygen, and should retain a cosmetically and esthetically pleasing appearance without loss of their coloring power.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

An agent for the oxidative dyeing and/or lightening of keratinic fibers, in particular human hair, includes in a cosmetic carrier: (a) at least one first alkyl glucoside of formula (I)

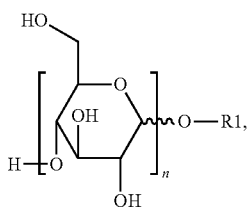

where R1 stands for an unbranched or branched, saturated or unsaturated $C_{20}$-$C_{28}$ alkyl group and n stands for an integer from 1 to 10; (b) at least one second alkyl glucoside of formula (II)

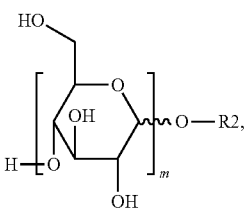

where R2 stands for an unbranched or branched, saturated or unsaturated $C_8$-$C_{18}$ alkyl group and m stands for an integer from 1 to 10; (c) at least one oxidation dye precursor of the developer type; and (d) at least one oxidation dye precursor of the coupler type.

The invention is also directed to the use of the combination of (a) at least one first alkyl glucoside of formula (I)

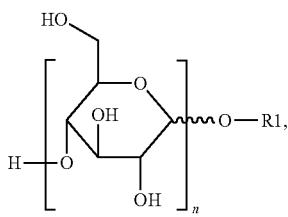

where R1 stands for an unbranched or branched, saturated or unsaturated $C_{20}$-$C_{28}$ alkyl group and n stands for an integer from 1 to 10; and (b) at least one second alkyl glucoside of formula (II)

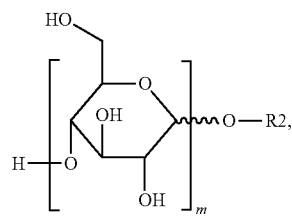

where R2 stands for an unbranched or branched, saturated or unsaturated $C_8$-$C_{18}$ alkyl group and m stands for an integer from 1 to 10, for preventing the discoloration, caused by atmospheric oxygen, of agents for oxidative dyeing and/or lightening of keratinic fibers, which include; (c) at least one oxidation dye precursor of the developer type; and (d) at least one oxidation dye precursor of the coupler type in a cosmetic carrier.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

In the course of the studies leading to the present invention, it has surprisingly been found that it is possible to effectively minimize the autoxidation of oxidation dye precursors when the agents include, in addition to the oxidation dye precursors of the developer type and of the coupler type, specific combinations of two different alkyl glucosides having different alkyl chain lengths.

A first subject matter of the present invention is an agent for dyeing and/or lightening of keratinic fibers, in particular human hair, that includes in a cosmetic carrier (a) at least one first alkyl glucoside of formula (I)

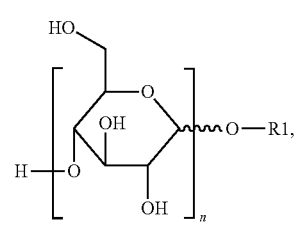

where R1 stands for an unbranched or branched, saturated or unsaturated $C_{20}$-$C_{28}$ alkyl group and
n stands for an integer from 1 to 10,
(b) at least one second alkyl glucoside of formula (II)

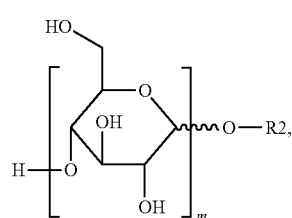

where R2 stands for an unbranched or branched, saturated or unsaturated $C_8$-$C_{18}$ alkyl group and m stands for an integer from 1 to 10, (c) at least one oxidation dye precursor of the developer type, and (d) at least one oxidation dye precursor of the coupler type.

Keratin-containing fibers are understood in principle to mean all animal hair, for example wool, horsehair, Angora hair, fur, feathers, and products or textiles manufactured therefrom. However, the keratinic fibers are preferably human hair.

The term "agent for dyeing and/or lightening" of keratin fibers used according to the invention is understood to mean oxidative coloring agents used according to the invention. Oxidative coloring agents include oxidation dye precursors, so-called developer and coupler components. Developers and couplers diffuse separately into the keratin fiber, and form the actual dyes in a chemical reaction with one another, under the influence of an alkalizing agent (ammonia, for example) and an oxidizing agent (usually hydrogen peroxide). Depending on the quantity of oxidizing agent used, the keratin fiber at the same time is more or less intensely lightened during the coloring, since the oxidizing agent not only initiates the dye formation process of the developers and couplers, but also oxidatively destroys the pigments (melanins) inherent in the hair.

Depending on the quantities of the oxidation dye precursors and of the oxidizing agent used, the oxidative coloration may therefore primarily be a coloration (with a high component of dye) or primarily a lightening (with a high component of oxidizing agent). In the latter case, the oxidation dye precursors are mainly used for shading of the lightening result.

The agents according to the invention include the components which are important to the invention in a cosmetic carrier, preferably in a suitable aqueous, alcoholic, or aqueous-alcoholic carrier. For purposes of the hair dyeing, such carriers, for example creams, emulsions, gels, or also surfactant-containing foaming solutions, for example shampoos, foam aerosols, foam formulations, or other preparations, are suitable for application to the hair.

As the first important formulation component, the agents according to the invention include at least one alkyl glucoside (a) of formula (I)

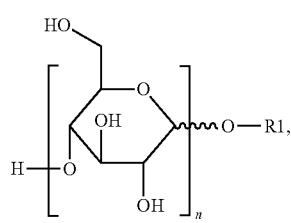
(I)

where R1 stands for an unbranched or branched, saturated or unsaturated $C_{20}$-$C_{28}$ alkyl group and n stands for an integer from 1 to 10.

An unbranched alkyl group is understood to mean a linear alkyl group.

Within the meaning of the present invention, alkyl glucosides are understood to mean the glycosides of glucose, wherein the formation of the glycosidic bond in the form of a condensation reaction, starting from the anomeric hydroxy group of the glucose radical (in the present case, in its pyranose form), takes place with the alcoholic OH group of a $C_{20}$-$C_{28}$ alkanol.

The glycosidic functionality is formed starting from glucose in its pyranose form, wherein the glucosides starting from α-glucose (formula Ia) as well as starting from β-glucose (formula Ib) are encompassed by the invention.

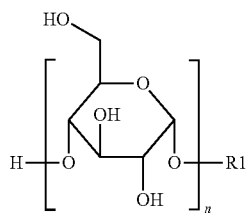
(Ia)

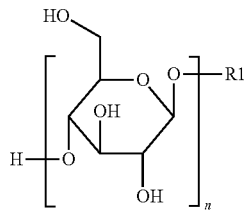
(Ib)

The radical R1 stands for an unbranched or branched, saturated or unsaturated $C_{20}$-$C_{28}$ alkyl group, and n stands for an integer from 1 to 10.

It has been found that the autoxidation caused by atmospheric oxygen may be efficiently minimized in particular when the radical R1 stands for an unbranched saturated $C_{20}$-$C_{24}$ alkyl group, preferably for an unbranched saturated $C_{20}$-$C_{22}$ alkyl group, and very particularly preferably for an unbranched saturated $C_{20}$ alkyl group.

Furthermore, the stated object of the invention is optimally achieved in particular when n stands for a number from 1 to 4, preferably for the number 1 or 2, and very particularly preferably for the number 1.

Compound (Ic) is very particularly preferably used as the alkyl glucoside of formula (I).

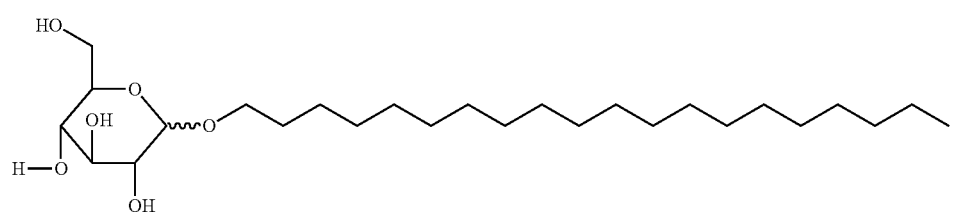
(Ic)

In one particularly preferred embodiment, an agent for dyeing and/or lightening of keratinic fibers is therefore characterized in that it includes as the first alkyl glucoside (a) at least one compound of formula (I), in which R1 stands for an unbranched saturated $C_{20}$ alkyl group and n stands for the number 1.

A correspondingly particularly preferred alkyl glucoside (a) where R1 is a $C_{20}$ alkyl group is known, for example, under the trade name Montanov 202.

The reduction of the autoxidation is also effective in particular when the alkyl glucoside(s) (a) of formula (I) is/are used in certain quantity ranges. The alkyl glucoside(s) of formula (I) is/are particularly preferably used in a total quantity of 0.3 to 4.5% by weight, preferably 0.5 to 3.5% by weight, more preferably 0.7 to 2.5% by weight, and particularly preferably 0.9 to 1.5% by weight, in each case based on the total weight of the ready-to-apply agent.

In another particularly preferred embodiment, an agent according to the invention is therefore characterized in that it includes one or more alkyl glucosides (a) of formula (I) in a total quantity of 0.3 to 4.5% by weight, preferably 0.5 to 3.5% by weight, more preferably 0.7 to 2.5% by weight, and particularly preferably 0.9 to 1.5% by weight, based on the total weight of the ready-to-apply agent.

As the second important formulation component, the agents according to the invention include at least one further alkyl glucoside (b) of formula (II)

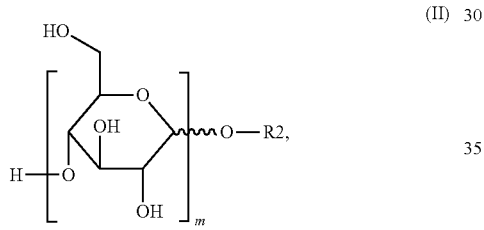

(II)

where R2 stands for an unbranched or branched, saturated or unsaturated $C_8$-$C_{18}$ alkyl group and m stands for an integer from 1 to 10.

The formation of glucosides of formula (II) also takes place starting from glucose in its pyranose form, wherein here as well, the glucosides starting from α-glucose (formula IIa) as well as starting from β-glucose (formula IIb) are encompassed by the invention.

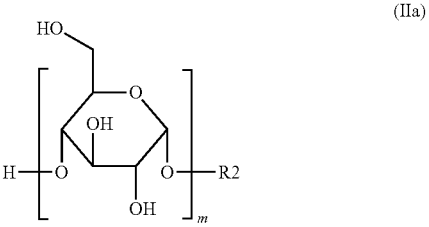

(IIa)

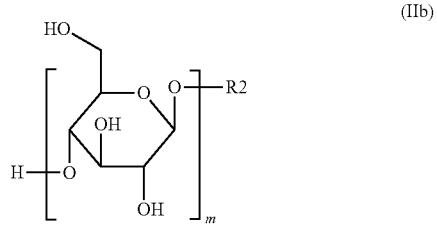

(IIb)

When selected representatives of alkyl glucosides of formula (II) together with the other important components (a), (c), and (d) are used in the agent according to the invention, the corresponding agents are particularly insensitive to atmospheric oxygen, and discolor little under its influence.

It is therefore preferred when the radical R2 stands for an unbranched saturated $C_{12}$-$C_{18}$ alkyl group. The radical R2 more preferably stands for an unbranched saturated $C_{14}$-$C_{16}$ alkyl group, and the radical R2 very particularly preferably stands for an unbranched saturated $C_{16}$-$C_{18}$ alkyl group.

Furthermore, for achieving the stated object, it is advantageous when m stands for an integer from 1 to 4, m more preferably stands for the number 1 or 2, and m explicitly particularly preferably stands for the number 1.

At least one compound selected from formulas (IIc) and (IId) is very particularly preferred as the alkyl glucoside of formula (II).

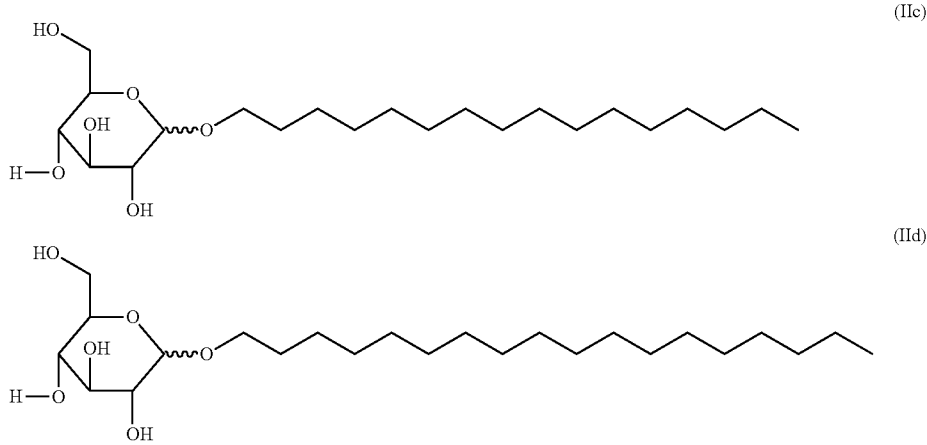

(IIc)

(IId)

In another particularly preferred embodiment, an agent according to the invention is characterized in that it includes at least one compound of formula (II) as the second alkyl glucoside (b), in which R2 stands for an unbranched saturated $C_{16}$ alkyl group or an unbranched saturated $C_{18}$ alkyl group and m stands for the number 1.

One particularly preferred alkyl glucoside (b) where R2 is a $C_{16}$-$C_{18}$ alkyl group is known, for example, under the trade name Montanov 68.

With regard to optimally achieving the stated object according to the invention, the alkyl glucoside(s) of formula (II) is/are preferably included in the agent according to the invention in certain quantity ranges. It is particularly preferred when the agent according to the invention includes one or more alkyl glucosides (b) of formula (II) in a total quantity of 1.2 to 8.0% by weight, preferably 1.6 to 6.5% by weight, more preferably 2.0 to 5.0% by weight, and particularly preferably 2.4 to 3.5% by weight, based on the total weight of the ready-to-apply agent.

In another particularly preferred embodiment, an agent according to the invention is therefore characterized in that it includes one or more alkyl glucosides (b) of formula (II) in a total quantity of 1.2 to 8.0% by weight, preferably 1.6 to 6.5% by weight, more preferably 2.0 to 5.0% by weight, and particularly preferably 2.4 to 3.5% by weight, based on the total weight of the ready-to-apply agent.

Furthermore, it has been found that the coloring agents according to the invention change color less, in particular in the presence of atmospheric oxygen, when the alkyl glucosides of formula (I) and the alkyl glucosides of formula (II) are used in certain quantity ratios relative to one another.

In this regard, it is particularly advantageous when the total quantity of alkyl glucosides of formula (II) used in the ready-to-apply agent is at least twice the total quantity of the alkyl glucosides of formula (I) included in the ready-to-apply agent.

In another very particularly preferred embodiment, an agent according to the invention is therefore characterized in that the quantity ratio of all alkyl glucosides of formula (I) included in the ready-to-apply agent to all alkyl glucosides of formula (II) included in the ready-to-apply agent is 1:2 to 1:10. preferably 1:2 to 1:5.

As the third important formulation component (c), the agents according to the invention for dyeing and/or lightening of keratin fibers include at least one oxidation dye precursor of the developer type.

Suitable oxidation dye precursors of the developer type are selected from at least one compound of the group p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxyl)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one, and the physiologically acceptable salts thereof.

In the course of the studies leading to the present invention, it has surprisingly been found that the specific combinations of alkyl glucosides of formula (I) and alkyl glucosides of formula (II) advantageously minimize the autoxidation of the agents according to the invention, in particular when the agents include p-toluylenediamine (2,5-diaminotoluene) as the oxidation dye precursor of the developer type.

In another particularly preferred embodiment, an agent according to the invention is therefore characterized in that it includes toluylenediamine (2,5-diaminotoluene) as the oxidation dye precursor of developer type (c).

Toluylenediamine (2,5-diaminotoluene) may be used in oxidative coloring agents in the form of its free base, or in the form of one of its physiological salts. Examples of physiologically acceptable salts are toluylenediamine (2,5-diaminotoluene) hydrochloride, toluylenediamine (2,5-diaminotoluene) hydrobromide, and toluylenediamine (2,5-diaminotoluene) sulfate.

It has been found that the autoxidation of agents according to the invention which include toluylenediamine (2,5-diaminotoluene) in the form of the sulfate salt may be suppressed in a particularly effective manner, and that corresponding formulations change color the least when they are exposed to atmospheric oxygen.

In another embodiment which is explicitly mentioned as being very particularly preferred, an agent according to the invention is therefore characterized in that it includes toluylenediamine (2,5-diaminotoluene) in the form of its sulfate salt (toluylenediamine (2,5-diaminotoluene) sulfate).

The autoxidation of the agents according to the invention may be efficiently and effectively suppressed in particular when certain quantities of the sulfate salt of p-toluylenediamine are used. The sulfate salt of p-toluylenediamine is therefore used in quantities of 0.45 to 1.45% by weight, preferably 0.55 to 1.35% by weight, more preferably 0.65 to 1.25% by weight, and particularly preferably 0.70 to 1.05% by weight, based on the total weight of the ready-to-apply agent.

The basis for calculation of the quantities of p-toluylenediamine sulfate used is the compound of the following structure, having a molar mass of 220.25 g/mol.

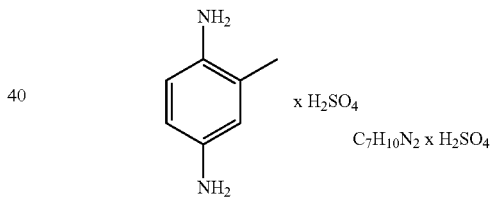

In another particularly preferred embodiment, an agent according to the invention is characterized in that it includes p-toluylenediamine, which is present in the form of its sulfate salt, in a quantity of 0.45 to 1.45% by weight, preferably 0.55 to 1.35% by weight, more preferably 0.65 to 1.25% by weight, and particularly preferably 0.70 to 1.05% by weight, based on the total weight of the ready-to-apply agent, as the oxidation dye precursor of developer type (c).

As the fourth important component (d), the agents according to the invention include at least one oxidation dye precursor of the coupler type.

Suitable oxidation dye precursors of the coupler type are selected from the group 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxyl)ethanol, 1,3-bis(2,4-diaminophenoxy) propane, 1-methoxy-2-amino-4-(2-hydroxyethylamino) benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)

ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-yl-phenyl)amino]ethanol, 3-amino-4-(2-methoxyethoxy)-5-methylphenylamine, 1-amino-3-bis(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methyl-amino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or mixtures of these compounds or their physiologically acceptable salts.

It has been found that the discoloration of the agents according to the invention may be effectively minimized in particular when very specific combinations of components (a), (b), and (c) with oxidation dye precursors of coupler type (d) are used in the agents according to the invention.

Particularly low discoloration caused by atmospheric oxygen has been observed with agents according to the invention which include one or more resorcinol derivatives selected from the group resorcinol, 2-methylresorcinol, and 4-chlororesorcinol as the oxidation dye precursor of the coupler type.

In another particularly preferred embodiment, an agent according to the invention is therefore characterized in that it includes one or more resorcinol derivatives selected from the group resorcinol, 2-methylresorcinol, and 4-chlororesorcinol as the oxidation dye precursor of the coupler type.

It is particularly advantageous when the resorcinol derivative(s) from the above-mentioned group is/are included in the agent according to the invention in specific quantity ranges.

In another particularly preferred embodiment, an agent according to the invention is characterized in that it includes one or more resorcinol derivatives selected from the group resorcinol, 2-methylresorcinol, and 4-chlororesorcinol in a total quantity of 0.10 to 0.85% by weight, preferably 0.15 to 0.75% by weight, more preferably 0.20 to 0.65% by weight, and particularly preferably 0.25 to 0.55% by weight, based on the total weight of the ready-to-apply agent, as the oxidation dye precursor of coupler type (d).

Furthermore, it has been found that the autoxidation of shadings in which m-aminophenol derivatives are used for dyeing the keratin fiber may also be advantageously minimized by using combinations of a first alkyl glucoside of formula (I) and a second alkyl glucoside of formula (II).

In another particularly preferred embodiment, the agents according to the invention therefore include as the oxidation dye precursor of coupler type (d) one or more m-aminophenol derivatives selected from the group m-aminophenol, 5-amino-2-methylphenol, and 3-amino-2-chloro-6-methylphenol.

It is likewise particularly advantageous when the m-aminophenol derivatives from the above-mentioned group are included in the agent according to the invention in specific quantity ranges.

In another particularly preferred embodiment, an agent according to the invention is characterized in that it includes one or more m-aminophenol derivatives selected from the group m-aminophenol, 5-amino-2-methylphenol, and 3-amino-2-chloro-6-methylphenol in a total quantity of 0.01 to 0.55% by weight, preferably 0.03 to 0.45% by weight, more preferably 0.05 to 0.35% by weight, and particularly preferably 0.07 to 0.25% by weight, based on the total weight of the ready-to-apply agent, as the oxidation dye precursor of coupler type (d).

Lastly, it has likewise been found that the autoxidation of shadings in which 2-aminopyridine derivatives are used for dyeing the keratin fiber may be advantageously minimized by using combinations of a first alkyl glucoside of formula (I) and a second alkyl glucoside of formula (II).

In another particularly preferred embodiment, the agents according to the invention therefore include one or more 2-aminopyridine derivatives selected from the group 3-amino-2-methylamino-6-methoxypyridine and 2-amino-3-hydroxypyridine as the oxidation dye precursor of coupler type (d).

It is likewise particularly advantageous when the 2-aminopyridine derivative(s) from the above-mentioned group is/are included in the agent according to the invention in specific quantity ranges.

In another particularly preferred embodiment, an agent according to the invention is characterized in that it includes one or more 2-aminopyridine derivatives selected from the group 3-amino-2-methylamino-6-methoxypyridine and 2-amino-3-hydroxypyridine in a total quantity of 0.001 to 0.35% by weight, preferably 0.005 to 0.25% by weight, more preferably 0.01 to 0.15% by weight, and particularly preferably 0.02 to 0.05% by weight, based on the total weight of the ready-to-apply agent, as the oxidation dye precursor of coupler type (d).

Taking into account the above-mentioned preferred and particularly preferred quantity ranges of components (a), (b), and (c) according to the invention and of the particularly preferred couplers and use quantities of coupler (d), a particularly preferred agent according to the invention is characterized in that it includes
(a) one or more alkyl glucosides of formula (I) in a total quantity of 0.3 to 4.5% by weight
(b) one or more alkyl glucosides of formula (II) in a total quantity of 1.2 to 8.0% by weight
(c) toluylenediamine sulfate in a quantity of 0.45 to 1.45% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.3 to 4.5% by weight
(b) one or more alkyl glucosides of formula (II) in a total quantity of 1.2 to 8.0% by weight
(c) toluylenediamine sulfate in a quantity of 0.65 to 1.25% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.3 to 4.5% by weight
(b) one or more alkyl glucosides of formula (II) in a total quantity of 1.2 to 8.0% by weight
(c) toluylenediamine sulfate in a quantity of 0.70 to 1.05% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.3 to 4.5% by weight
(b) one or more alkyl glucosides of formula (II) in a total quantity of 1.6 to 6.5% by weight
(c) toluylenediamine sulfate in a quantity of 0.55 to 1.35% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.3 to 4.5% by weight
(b) one or more alkyl glucosides of formula (II) in a total quantity of 1.6 to 6.5% by weight
(c) toluylenediamine sulfate in a quantity of 0.70 to 1.05% by weight as oxidation dye precursor of the developer type and
(d) at least one oxidation dye precursor of the coupler type, based on the total weight of the ready-to-apply agent Another particularly preferred agent is characterized in that it includes
(a) one or more alkyl glucosides of formula (I) in a total quantity of 0.3 to 4.5% by weight
(b) one or more alkyl glucosides of formula (II) in a total quantity of 2.0 to 5.0% by weight
(c) toluylenediamine sulfate in a quantity of 0.45 to 1.45% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.3 to 4.5% by weight
(b) one or more alkyl glucosides of formula (II) in a total quantity of 2.0 to 5.0% by weight
(c) toluylenediamine sulfate in a quantity of 0.65 to 1.25% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.3 to 4.5% by weight
(b) one or more alkyl glucosides of formula (II) in a total quantity of 2.4 to 3.5% by weight
(c) toluylenediamine sulfate in a quantity of 0.45 to 1.45% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.3 to 4.5% by weight
(b) one or more alkyl glucosides of formula (II) in a total quantity of 2.4 to 3.5% by weight
(c) toluylenediamine sulfate in a quantity of 0.55 to 1.35% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.3 to 4.5% by weight
(b) one or more alkyl glucosides of formula (II) in a total quantity of 2.4 to 3.5% by weight
(c) toluylenediamine sulfate in a quantity of 0.65 to 1.25% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.5 to 3.5% by weight
(b) one or more alkyl glucosides of formula (II) in a total quantity of 1.2 to 8.0% by weight
(c) toluylenediamine sulfate in a quantity of 0.45 to 1.45% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.5 to 3.5% by weight
(b) one or more alkyl glucosides of formula (II) in a total quantity of 1.2 to 8.0% by weight
(c) toluylenediamine sulfate in a quantity of 0.55 to 1.35% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.5 to 3.5% by weight
(b) one or more alkyl glucosides of formula (II) in a total quantity of 1.2 to 8.0% by weight
(c) toluylenediamine sulfate in a quantity of 0.65 to 1.25% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.5 to 3.5% by weight
(b) one or more alkyl glucosides of formula (II) in a total quantity of 1.6 to 6.5% by weight
(c) toluylenediamine sulfate in a quantity of 0.45 to 1.45% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.5 to 3.5% by weight
(b) one or more alkyl glucosides of formula (II) in a total quantity of 1.6 to 6.5% by weight
(c) toluylenediamine sulfate in a quantity of 0.55 to 1.35% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.5 to 3.5% by weight
(b) one or more alkyl glucosides of formula (II) in a total quantity of 1.6 to 6.5% by weight
(c) toluylenediamine sulfate in a quantity of 0.65 to 1.25% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.5 to 3.5% by weight
(b) one or more alkyl glucosides of formula (II) in a total quantity of 2.0 to 5.0% by weight
(c) toluylenediamine sulfate in a quantity of 0.45 to 1.45% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.5 to 3.5% by weight
(b) one or more alkyl glucosides of formula (II) in a total quantity of 2.0 to 5.0% by weight
(c) toluylenediamine sulfate in a quantity of 0.65 to 1.25% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.5 to 3.5% by weight
(b) one or more alkyl glucosides of formula (II) in a total quantity of 2.0 to 5.0% by weight
(c) toluylenediamine sulfate in a quantity of 0.70 to 1.05% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.5 to 3.5% by weight
(b) one or more alkyl glucosides of formula (II) in a total quantity of 2.4 to 3.5% by weight
(c) toluylenediamine sulfate in a quantity of 0.45 to 1.45% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.5 to 3.5% by weight
(b) one or more alkyl glucosides of formula (II) in a total quantity of 2.4 to 3.5% by weight
(c) toluylenediamine sulfate in a quantity of 0.65 to 1.25% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.5 to 3.5% by weight
(b) one or more alkyl glucosides of formula (II) in a total quantity of 2.4 to 3.5% by weight
(c) toluylenediamine sulfate in a quantity of 0.70 to 1.05% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.7 to 2.5% by weight
(b) one or more alkyl glucosides of formula (II) in a total quantity of 1.2 to 8.0% by weight
(c) toluylenediamine sulfate in a quantity of 0.55 to 1.35% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.7 to 2.5% by weight
(b) one or more alkyl glucosides of formula (II) in a total quantity of 1.2 to 8.0% by weight
(c) toluylenediamine sulfate in a quantity of 0.65 to 1.25% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.7 to 2.5% by weight
(b) one or more alkyl glucosides of formula (II) in a total quantity of 1.2 to 8.0% by weight
(c) toluylenediamine sulfate in a quantity of 0.70 to 1.05% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.7 to 2.5% by weight
(b) one or more alkyl glucosides of formula (II) in a total quantity of 1.6 to 6.5% by weight
(c) toluylenediamine sulfate in a quantity of 0.55 to 1.35% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.7 to 2.5% by weight
(b) one or more alkyl glucosides of formula (II) in a total quantity of 1.6 to 6.5% by weight
(c) toluylenediamine sulfate in a quantity of 0.65 to 1.25% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.7 to 2.5% by weight
(b) one or more alkyl glucosides of formula (II) in a total quantity of 2.0 to 5.0% by weight
(c) toluylenediamine sulfate in a quantity of 0.45 to 1.45% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.7 to 2.5% by weight
(b) one or more alkyl glucosides of formula (II) in a total quantity of 2.0 to 5.0% by weight
(c) toluylenediamine sulfate in a quantity of 0.55 to 1.35% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.7 to 2.5% by weight
(b) one or more alkyl glucosides of formula (II) in a total quantity of 2.0 to 5.0% by weight
(c) toluylenediamine sulfate in a quantity of 0.70 to 1.05% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.7 to 2.5% by weight
(b) one or more alkyl glucosides of formula (II) in a total quantity of 2.4 to 3.5% by weight
(c) toluylenediamine sulfate in a quantity of 0.55 to 1.35% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.7 to 2.5% by weight
(b) one or more alkyl glucosides of formula (II) in a total quantity of 2.4 to 3.5% by weight
(c) toluylenediamine sulfate in a quantity of 0.70 to 1.05% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.9 to 1.5% by weight
(b) one or more alkyl glucosides of formula (II) in a total quantity of 1.2 to 8.0% by weight
(c) toluylenediamine sulfate in a quantity of 0.45 to 1.45% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.9 to 1.5% by weight
(b) one or more alkyl glucosides of formula (II) in a total quantity of 1.2 to 8.0% by weight
(c) toluylenediamine sulfate in a quantity of 0.65 to 1.25% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.9 to 1.5% by weight
(b) one or more alkyl glucosides of formula (II) in a total quantity of 1.6 to 6.5% by weight
(c) toluylenediamine sulfate in a quantity of 0.55 to 1.35% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.9 to 1.5% by weight
(b) one or more alkyl glucosides of formula (II) in a total quantity of 1.6 to 6.5% by weight
(c) toluylenediamine sulfate in a quantity of 0.65 to 1.25% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.9 to 1.5% by weight
(b) one or more alkyl glucosides of formula (II) in a total quantity of 2.0 to 5.0% by weight
(c) toluylenediamine sulfate in a quantity of 0.45 to 1.45% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.9 to 1.5% by weight
(b) one or more alkyl glucosides of formula (II) in a total quantity of 2.0 to 5.0% by weight
(c) toluylenediamine sulfate in a quantity of 0.55 to 1.35% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.9 to 1.5% by weight
(b) one or more alkyl glucosides of formula (II) in a total quantity of 2.0 to 5.0% by weight
(c) toluylenediamine sulfate in a quantity of 0.70 to 1.05% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.9 to 1.5% by weight
(b) one or more alkyl glucosides of formula (II) in a total quantity of 2.4 to 3.5% by weight
(c) toluylenediamine sulfate in a quantity of 0.45 to 1.45% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.9 to 1.5% by weight
(b) one or more alkyl glucosides of formula (II) in a total quantity of 2.4 to 3.5% by weight
(c) toluylenediamine sulfate in a quantity of 0.65 to 1.25% by weight as oxidation dye precursor of the developer type and
(d) at least one oxidation dye precursor of the coupler type, based on the total weight of the ready-to-apply agent.

Another particularly preferred agent is characterized in that it includes
(a) one or more alkyl glucosides of formula (I) in a total quantity of 0.9 to 1.5% by weight
(b) one or more alkyl glucosides of formula (II) in a total quantity of 2.4 to 3.5% by weight
(c) toluylenediamine sulfate in a quantity of 0.70 to 1.05% by weight as oxidation dye precursor of the developer type and
(d) at least one oxidation dye precursor of the coupler type, based on the total weight of the ready-to-apply agent.

Also when certain combinations of oxidation dye precursors of coupler type (d) are used in the agents according to the invention, the autoxidation of the agents caused by atmospheric oxygen may be effectively minimized or even almost totally prevented.

Good results are obtained in particular when a combination of resorcinol and m-aminophenol is used as oxidation dyes of coupler type (d).

In another particularly preferred embodiment, an agent according to the invention is therefore characterized in that it includes resorcinol and m-aminophenol as oxidation dye precursors of coupler type (d).

Also when a combination of resorcinol and 3-amino-2-methylamino-6-methoxypyridine is used as oxidation dyes of coupler type (d), the change in color of the agents caused by atmospheric oxygen is particularly low.

In another particularly preferred embodiment, an agent according to the invention is therefore characterized in that it includes resorcinol and 3-amino-2-methylamino-6-methoxypyridine as oxidation dye precursors of coupler type (d).

In addition, with regard to minimizing autoxidation, it has been found to be particularly advantageous when the agents according to the invention include a combination of m-aminophenol and 3-amino-2-methylamino-6-methoxypyridine as oxidation dye precursors of coupler type (d).

In another particularly preferred embodiment, an agent according to the invention is therefore characterized in that it includes m-aminophenol and 3-amino-2-methylamino-6-methoxypyridine as oxidation dye precursors of coupler type (d).

When resorcinol together with m-aminophenol and 3-amino-2-methylamino-6-methoxypyridine are used as oxidation dye precursors of coupler type (d), the discoloration of the agents caused by atmospheric oxygen may likewise be suppressed particularly well in interaction with the other important ingredients (a), (b), and (c).

In another particularly preferred embodiment, an agent according to the invention is therefore characterized in that it includes resorcinol, m-aminophenol, and 3-amino-2-methylamino-6-methoxypyridine as oxidation dye precursors of coupler type (d).

In the course of the studies leading to the present invention, it has been found that the extent to which the autoxidation of the oxidation dye precursors in the agents according to the invention may be reduced or inhibited is based on an interaction of the important components (a) and (b) on the one hand, and the important components (c) and (d) on the other hand.

Consequently, the autoxidation may be optimally inhibited when the total quantity of alkyl gluco sides (a) and (b) included in the ready-to-apply agent is in an optimal ratio to the total quantity of oxidation dye precursors (c) and (d) present in the ready-to-apply agent.

It has been found that effective prevention of autoxidation may be observed in particular when the total quantity of alkyl glucosides (a) and (b) included in the agent is at least as great as the total quantity of all oxidation dye precursors (c) and (d) included in the ready-to-apply agent. The total quantity of alkyl glucosides (a) and (b) included in the agent is preferably at least twice as great as the total quantity of all oxidation dye precursors (c) and (d) included in the ready-to-apply agent. In particular, the total quantity of alkyl glucosides (a) and (b) included in the agent is preferably at least three times as great as the total quantity of all oxidation dye precursors (c) and (d) included in the ready-to-apply agent.

In another very particularly preferred embodiment, an agent according to the invention is therefore characterized in that the quantity ratio of all oxidation dye precursors included in the ready-to-apply agent to all alkyl glucosides included in the ready-to-apply agent is at least 1:1, preferably at least 1:2, and particularly preferably at least 1:3.

The ready-to-apply coloring agents may also include additional active substances, auxiliary substances, and additives to improve the coloring power and to adjust further desired properties of the agents.

The ready-to-apply coloring agents are preferably provided as a liquid preparation, and therefore a surface-active substance is additionally added to the agents; such surface-active substances may be referred to as surfactants or as emulsifiers, depending on the field of application. They are preferably selected from anionic, cationic, zwitterionic, amphoteric, and nonionic surfactants and emulsifiers.

Agents which are preferred according to the invention are characterized in that the agent additionally includes at least one anionic surfactant. Preferred anionic surfactants are fatty acids, alkyl sulfates, alkyl ether sulfates, and ether carboxylic acids having 10 to 20 C atoms in the alkyl group and up to 16 glycol ether groups in the molecule. The anionic surfactants are used in proportions of 0.1 to 45% by weight, preferably 1 to 30% by weight, and very particularly preferably 1 to 15% by weight, based on the total quantity of the ready-to-apply agent.

Agents which are preferred according to the invention are characterized in that the agent additionally includes at least one zwitterionic surfactant. Preferred zwitterionic surfactants are betaines, N-alkyl-N,N-dimethylammonium glycinates, N-acylaminopropyl-N,N-dimethylammonium glycinates, and 2-alkyl-3-carboxymethyl-3-hydroxyethyl imidazolines. One preferred zwitterionic surfactant is known under the INCI name Cocamidopropyl Betaine.

Agents which are preferred according to the invention are characterized in that the agent additionally includes at least one amphoteric surfactant. Preferred amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids, and alkylaminoacetic acids. Particularly preferred amphoteric surfactants are N-cocoalkylaminopropionate, cocoacylaminoethylaminopropionate, and $C_{12}$-$C_{18}$ acyl sarcosine.

In addition, it has proven to be advantageous when the agents include further nonionogenic surface-active substances. Examples of preferred nonionic surfactants are alkylene oxide addition products with fatty alcohols and fatty acids, in each case having 2 to 30 mol ethylene oxide per mol of fatty alcohol or fatty acid. Preparations having excellent properties are likewise obtained when they include fatty acid esters of ethoxylated glycerin as nonionic surfactants.

The nonionic, zwitterionic, or amphoteric surfactants are used in proportions of 0.1 to 45% by weight, preferably 1 to 30% by weight, and very particularly preferably 1 to 15% by weight, based on the total quantity of the ready-to-apply agents.

Agents which are suitable according to the invention may also include cationic surfactants of the quaternary ammonium compound, esterquat, and amidoamine type. Preferred quaternary ammonium compounds are ammonium halides, and the imidazolium compounds known under the INCI names Quaternium-27 and Quaternium-83. Quaternized protein hydrolysates represent further cationic surfactants which are usable according to the invention. The stearamidopropyl dimethylamine which is obtainable under the name TEGO® Amid S 18 represents a compound from the group of amidoamines which is particularly suitable according to the invention. Preferred esterquats are quaternized ester salts of fatty acids with triethanolamine, quaternized ester salts of fatty acids with diethanolalkylamines, and quaternized ester salts of fatty acids with 1,2-dihydroxypropyldialkylamines. The cationic surfactants are preferably included in the agents used according to the invention in proportions of 0.05 to 10% by weight, based on the overall agent.

The ready-to-apply coloring agents may include further auxiliary substances and additives. Thus, it has proven to be advantageous when the agents include at least one thickener. In principle, there are no limitations with regard to these thickeners. Organic as well as strictly inorganic thickeners may be used.

Suitable thickeners are anionic synthetic polymers; cationic synthetic polymers; naturally occurring thickeners, such as nonionic guar gums, scleroglucan gums, or xanthan gums, gum arabic, gum ghatti, karaya gum, gum tragacanth, carrageenan gum, agar-agar, locust bean gum, pectins, alginates, starch fractions, and derivatives such as amylose, amylopectin, and dextrins, and cellulose derivatives such as methylcellulose, carboxyalkyl celluloses, and hydroxyalkyl celluloses; nonionic synthetic polymers such as polyvinyl alcohol or polyvinylpyrrolidinone; and inorganic thickeners, in particular layered silicates such as bentonite, in particular smectites such as montmorillonite or hectorite.

Zwitterionic polymers may also be included in the agents according to the invention.

Preferred zwitterionic polymers are selected from the group of
  copolymers of dimethyldiallylammonium salts and acrylic acid, for example Polyquaternium-22,
  copolymers of dimethyldiallylammonium salts and methacrylic acid,
  copolymers of N,N,N-trimethyl-3-[(2-methyl-1-oxo-2-propen-1-yl)amino]-1-propanaminium salts and acrylic acid,
  copolymers of N,N,N-trimethyl-3-[(2-methyl-1-oxo-2-propen-1-yl)amino]-1-propanaminium salts and methacrylic acid,
  copolymers of N,N,N-trimethyl-2-[(2-methyl-1-oxo-2-propen-1-yl)amino]-1-ethanaminium salts and acrylic acid,
  copolymers of N,N,N-trimethyl-2-[(2-methyl-1-oxo-2-propen-1-yl)amino]-1-ethanaminium salts and methacrylic acid,
  copolymers of N,N,N-trimethyl-3-[(2-methyl-1-oxo-2-propen-1-yl)amino]-1-propanaminium salts, acrylic acid, and acrylamide, for example Polyquaternium-53,
  copolymers of N,N,N-trimethyl-3-[(2-methyl-1-oxo-2-propen-1-yl)amino]-1-propanaminium salts, methacrylic acid, and acrylamide,
  copolymers of 1-ethenyl-3-methyl-1H-imidazolium salts, 1-ethenyl-1H-imidazole, 1-ethenyl-2-pyrrolidinone, and methacrylic acid, for example Polyquaternium-86,
  copolymers of 1-ethenyl-3-methyl-1H-imidazolium salts, 1-ethenyl-1H-imidazole, 1-ethenyl-2-pyrrolidinone, and acrylic acid.

Mixtures of the above-mentioned preferred zwitterionic polymers (c) may also be included in the agents according to the invention.

In addition, it has been shown that the stated object according to the invention may in particular be achieved completely and satisfactorily when the agents according to the invention include further selected formulation components.

It has thus been found that the additional presence of certain higher-chain fatty alcohols even further improves the coloring result of the compositions according to the invention. It is therefore preferred when the agents according to the invention additionally include one or more fatty alcohols from the group arachidyl alcohol (eicosan-1-ol), gadoleic alcohol ((9Z)-eicos-9-en-1-ol), arachidonic alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and brassidyl alcohol ((13E)-docosen-1-01).

Particularly suitable agents include one or more higher-chain alcohols of the above-mentioned group in a total quantity of 1.0 to 10.0% by weight, preferably 1.4 to 8.0% by weight, more preferably 1.8 to 6.0% by weight, and particularly preferably 2.0 to 4.0% by weight, based on the total weight of the ready-to-apply agent.

In another preferred embodiment, an agent according to the invention is therefore characterized in that it additionally includes one or more fatty alcohols from the group arachidyl alcohol (eicosan-1-ol), gadoleic alcohol ((9Z)-eicos-9-en-1-ol), arachidonic alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and brassidyl alcohol ((13E)-docosen-1-ol) in a total quantity of 0.1 to 10.0% by weight, preferably 1.4 to 8.0% by weight, more preferably 1.8 to 6.0% by weight, and particularly preferably 2.0 to 4.0% by weight, based on the total weight of the ready-to-apply agent.

Dyeing processes on keratin fibers customarily take place in an alkaline environment. However, to protect the keratin fibers and also the skin to the greatest extent possible, setting an excessively high pH is not desirable. It is therefore preferred when the pH of the ready-to-apply agent is between 6 and 11, in particular between 7 and 10.5. pH values in the sense of the present invention are pH values that have been measured at a temperature of 22° C.

The alkalizing agents that are usable according to the invention for setting the preferred pH may be selected from the group comprising ammonia, alkanolamines, basic amino acids, and inorganic alkalizing agents such as alkaline earth or alkali metal hydroxides, alkaline earth or alkali metal metasilicates, alkaline earth or alkali metal phosphates, and alkaline earth or alkali metal hydrogen phosphates. Preferred inorganic alkalizing agents are magnesium carbonate, sodium hydroxide, potassium hydroxide, sodium silicate, and sodium metasilicate. Organic alkalizing agents that are usable according to the invention are preferably selected from monoethanolamine, 2-amino-2-methylpropanol, and triethanolamine. The basic amino acids that are usable as alkalizing agents according to the invention are preferably selected from the group comprising arginine, lysine, ornithine, and histidine, particularly preferably arginine.

It has proven to be advantageous when the oxidizing agent preparations according to the invention additionally include at least one stabilizer or complexing agent for stabilizing the hydrogen peroxide. Particularly preferred stabilizers are in particular EDTA and EDDS, and phosphonates, in particular 1-hydroxyethane-1,1-diphosphonate (HEDP) and/or ethylenediamine tetramethylene phosphonate (EDTMP) and/or diethylenetriamine pentamethylene phosphonate (DTPMP) or the sodium salts thereof.

To achieve an enhanced lightening and bleaching action, the agent may additionally include at least one peroxo salt. Suitable peroxo salts are inorganic peroxo compounds, preferably selected from the group comprising ammonium peroxodisulfate, alkali metal peroxodisulfates, ammonium peroxomonosulfate, alkali metal peroxomonosulfates, alkali metal peroxodiphosphates, and alkaline earth metal peroxides. Peroxodisulfates are particularly preferred, in particular ammonium peroxodisulfate, potassium peroxodisulfate, and sodium peroxodisulfate.

The persulfates are included in the agent according to the invention in each case in a quantity of 0.5 to 20% by weight, preferably 1 to 12.5% by weight, particularly preferably 2.5 to 10% by weight, and in particular 3 to 6% by weight, based on the total weight of the ready-to-apply agent.

Those skilled in the art will select these further substances according to the desired properties of the agents. With regard to further optional components and the quantities of these components used, express reference is made to relevant handbooks known to those skilled in the art. The additional active substances and auxiliary substances are preferably used in the agents according to the invention in each case in quantities of 0.0001 to 25% by weight, in particular 0.0005 to 15% by weight, based on the total weight of the application mixture.

In addition to the ingredients (a), (b), and (c) according to the invention, the agents according to the invention may also include reducing agents. Suitable reducing agents are sulfites such as sodium sulfite, potassium sulfite, sodium bisulfite, or potassium bisulfite. Ascorbic acid, isoascorbic acid, or dehydoascorbic acid are also suitable in this regard.

Although with regard to the prevention of autoxidation of the oxidation dye precursors it is advantageous to add reducing agents to the agents according to the invention, their use is also associated with disadvantages relating to application. If reducing agents are used in excessively large quantities, this may have adverse effects on the coloring power and color intensity, for example.

The total quantity of reducing agents used, to the extent possible, is therefore below 0.5% by weight, preferably below 0.3% by weight, and particularly preferably below 0.2% by weight, based on the total quantity of the ready-to-apply agent.

In another preferred embodiment, an agent according to the invention is therefore characterized in that it includes reducing agent, selected from the group sodium sulfite, sodium bisulfite, potassium sulfite, potassium bisulfite, ascorbic acid, and isoascorbic acid, in a total quantity of less than 0.5% by weight, preferably less than 0.3% by weight, and particularly preferably less than 0.2% by weight, based on the total weight of the ready-to-apply agent.

In addition to the above-mentioned ingredients, the agents according to the invention may also include the ingredients which are customary for oxidative dyes and lighteners. In addition to the oxidation dye precursors, the agents may therefore also include direct dyes, wherein these direct dyes may be selected from cationic, anionic, and nonionic dyes.

The agents according to the invention are agents for the oxidative dyeing and/or lightening of hair. In the ready-to-apply agent, the oxidation dye precursors react with the oxidizing agent to form the actual dyes. For this reason, the agents according to the invention are customarily packaged as multi-component agents, usually as two-component agents. The first component (A) includes the oxidation dye precursors (c) and (d), which shortly before application are mixed with a second component that includes the oxidizing agent (preparation B). The two components are usually mixed with one another in a 1:3 to 3:1 ratio. This mixture of the component that includes color cream and optionally alkalizing agent (preparation A) and the component that includes oxidizing agent (preparation B) is referred to as the application mixture or the ready-to-apply agent. In one preferred embodiment, the alkylglucosides of formulas (I) and (II) are likewise included in the first component (preparation A). All stated quantities with regard to the "ready-to-apply agent" refer to the ready-to-apply mixture of the component that includes color cream/alkalizing agent and the component that includes oxidizing agent.

A further subject matter of the present invention is a ready-to-apply agent for dyeing and/or lightening of keratinic fibers, characterized in that it is produced immediately prior to application by mixing preparations (A) and (B), wherein preparation (A) is an agent of the first subject matter of the invention, preparation (B) is an agent which includes hydrogen peroxide in a cosmetic carrier, and the ready-to-apply agent which is produced by mixing preparations (A) and (B) includes hydrogen peroxide in a quantity of 0.5 to 8.0% by weight, preferably 1.5 to 6.5% by weight, more preferably 2.2 to 4.5% by weight, and particularly preferably 3.2 to 3.8% by weight (calculated as 100% hydrogen peroxide), based on the total weight of the ready-to-apply agent.

The alkyl glucosides of formula (I) and alkyl glucosides of formula (II) included in the agent according to the invention are very well suited for preventing the autoxidation of oxidative agents for dyeing and/or lightening of keratinic fibers, which in a particular preferred embodiment include oxidation dyes of the developer type and of the coupler type.

A further subject matter of the present invention is the use of the combination of (a) at least one first alkyl glucoside of formula (I)

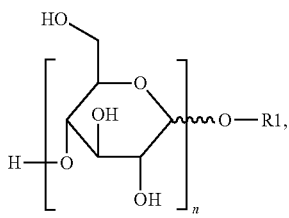

where R1 stands for an unbranched or branched, saturated or unsaturated $C_{20}$-$C_{28}$ alkyl group and
n stands for an integer from 1 to 10, and
(b) at least one second alkyl glucoside of formula (II)

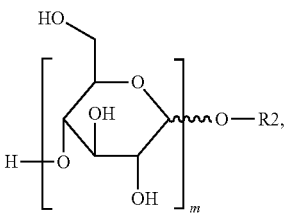

where R2 stands for an unbranched or branched, saturated or unsaturated $C_8$-$C_{18}$ alkyl group and
m stands for an integer from 1 to 10,
for preventing the discoloration, caused by atmospheric oxygen, of agents for oxidative dyeing and/or lightening of keratinic fibers, which include
(c) at least one oxidation dye precursor of the developer type and
(d) at least one oxidation dye precursor of the coupler type in a cosmetic carrier.

Atmospheric oxygen is understood to mean the oxygen (02) that is present in gaseous form in the atmosphere (air, gaseous mixture of the earth's atmosphere).

With regard to further preferred embodiments of the methods and uses according to the invention, the statements concerning agents according to the invention apply mutatis mutandis.

Examples

1. Preparation of the Ready-to-Apply Coloring Agents

The following formulations were prepared. The quantity statements are understood in each case to mean percent by weight unless noted otherwise.

| Formulation component | V1 (wt.-%) | E1 (wt.-%) |
|---|---|---|
| Montanov 68 (Cetearyl Alcohol, Cetearyl Glucoside) | — | 6.00 |
| Montanov 202 (Arachidyl Alcohol, Behenyl Alcohol, Arachidyl Glucoside) | — | 2.00 |
| Paraffinium liquidum | 7.40 | 7.40 |
| Lanette 22 (INCI: Behenyl Alcohol) | 1.80 | 1.80 |
| Lanette D (INCI: Cetearyl Alcohol) | 1.30 | 1.30 |
| Eumulgin B 3 (INCI: Ceteareth-30) | 1.30 | 1.30 |
| Product W 37194 (N,N,N-trimethyl-3-[(1-oxo-2-propenyl)amino]-1-propanaminium chloride, polymer with sodium 2-propenoate) (INCI: Acrylamidopropyl-trimonium Chloride/Acrylate Copolymer) | 2.00 | 2.00 |
| p-Toluylenediamine sulfate | 1.50 | 1.50 |
| Resorcinol | 0.58 | 0.58 |
| m-Aminophenol | 0.16 | 0.16 |
| 3-Amino-2-methylamino-6-methoxypyridine | 0.05 | 0.05 |
| Potassium hydroxide (50%) | 0.7 | 0.7 |
| Vitamin C | 0.05 | 0.05 |
| 60% hydroxyethane-1,1-diphosphonic acid | 0.20 | 0.20 |
| Sodium silicate 42 (3.1 $SiO_2$:$Na_2O$) | 0.5 | 0.5 |
| Ammonia (25% by weight aqueous solution) | 5.80 | 5.80 |
| Fragrance | 0.40 | 0.40 |
| Water | ad 100 | ad 100 |

V1 is a comparative formulation, and E1 is a formulation according to the invention. The color creams were mixed in each case in a 1:1 ratio with the following oxidizing agent formulation (OX):

| Formulation component | OX (wt.-%) |
|---|---|
| 85% phosphoric acid | 0.04 |
| Hydrogen peroxide (50%, aqueous solution) | 12.00 |
| Emulgade F (INCI: Cetearyl Alcohol, PEG-40 Castor Oil, Sodium Cetearyl Sulfate) | 2.10 |
| Sodium benzoate | 0.04 |
| Disodium pyrophosphate | 0.30 |
| Ethylenediamine tetraacetate, disodium salt | 0.15 |
| Water | ad 100 |

2. Measurement of the Autoxidation of the Color Creams

In each case 25 g of the previously prepared color creams (V1, E1) was spread onto Petri dishes and allowed to stand in air for a period of 60 minutes. The coloration of each application mixture was visually assessed after a period of 0 minutes (directly after spreading), and after 10 min, 20 min, 30 min, 40 min, and 60 min

TABLE 1

| | Coloration of the color creams | |
|---|---|---|
| Time period [min] | V1 Coloration (color intensity) | E1 Coloration (color intensity) |
| 0 | beige (−) | colorless (−) |
| 10 | dark beige (+) | colorless (−) |
| 20 | light brown (++) | beige (+) |
| 30 | medium brown (++) | beige-brown (+) |
| 40 | medium brown (++) | light brown (+) |
| 60 | medium brown (++) | light brown (+) |

Color intensity: + = low ++ = medium +++ = high
Over the entire observed period, the agent according to the invention (E1) was less intensely colored than the comparative formulation (V1).

3. Measurement of the Autoxidation of the Application Mixtures

In each case 25 g of the previously prepared application mixtures (V1+OX, E1+OX) was spread onto Petri dishes and allowed to stand in air for a period of 60 minutes. The coloration of each application mixture was visually assessed after a period of 0 minutes (directly after spreading), and after 10 min, 20 min, 30 min, 40 min, and 60 min.

TABLE 2

Coloration of the application mixture

| Time period [min] | V1 + OX Coloration (color intensity) | E1 + OX Coloration (color intensity) |
|---|---|---|
| 0 | light brown (+) | light beige (+) |
| 10 | medium brown (++) | beige (+) |
| 20 | medium brown (++) | medium beige (+) |
| 30 | dark brown (+++) | beige-brown (++) |
| 40 | dark brown (+++) | beige-brown (++) |
| 60 | very dark brown (+++) | brown (++) |

Color intensity: + = low ++ = medium +++ = high
Over the entire observed period, the agent according to the invention (E1 + OX) was less intensely colored than the comparative formulation (V1 + OX).

4. Coloration and Determination of the Color Intensity

The previously prepared application mixtures were applied to hair strands (buffalo stomach hair and hair from Kerling, natural white), using an applicator, and were left there for a period of 10 to 30 minutes. The application mixture was subsequently washed out with a shampoo and dried. The hair strands were then colorimetrically measured (measurement of the Lab value).

In the colorimetric measurement, the L value indicates the lightness of a strand, the value range for L extending from 0 to 100. The lower the L value, the darker the measured hair strand (L=0 means black, L=100 means (diffuse) white).

The following L values were measured:

TABLE 3

L values, buffalo stomach hair

| | Duration of application 10 min | Duration of application 20 min | Duration of application 30 min |
|---|---|---|---|
| V1 + OX | 26.78 | 18.98 | 16.35 |
| E1 + OX | 23.96 | 17.14 | 15.17 |

TABLE 4

L values, Kerling natural white

| | Duration of application 10 min | Duration of application 20 min | Duration of application 30 min |
|---|---|---|---|
| V1 + OX | 29.29 | 22.39 | 20.29 |
| E1 + OX | 27.03 | 17.85 | 17.49 |

The L values of the colorations obtained using the agent according to the invention (E1+OX), regardless of the duration of application, were consistently lower than those measured for the application of the comparative formulation (V1+OX). This means that the color of the hair dyed using the agent according to the invention had a darker or more intense shade.

The discoloration of the agents according to the invention themselves (discoloration of the formulations) was less; however, using the agents according to the invention it was still possible to achieve more intense colorations on the hair.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A ready to apply agent for the oxidative dyeing and/or lightening of keratinic fibers, including in a cosmetic carrier
   (a) 0.3 to 4.5% by weight at least one first alkyl glucoside of formula (I)

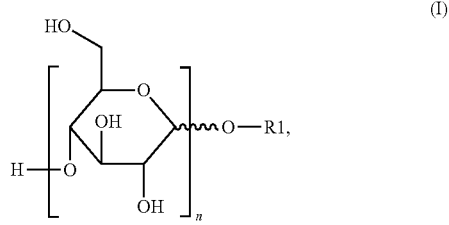

wherein R1 stands for an unbranched or branched, saturated or unsaturated $C_{20}$-$C_{28}$ alkyl group and n stands for an integer from 1 to 10,
   (b) 1.2 to 8.0% by weight at least one second alkyl glucoside of formula (II)

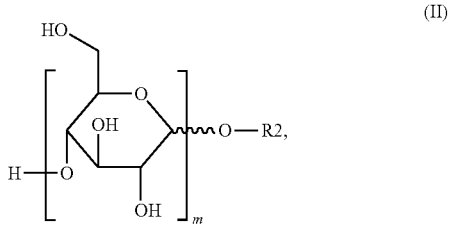

wherein R2 stands for an unbranched or branched, saturated or unsaturated $C_8$-$C_{18}$ alkyl group and m stands for an integer from 1 to 10,
   (c) at least one oxidation dye precursor of the developer type,
   (d) at least one oxidation dye precursor of the coupler type, and
   (e) an oxidizing agent,
   wherein a ratio of all alkyl glucosides of formula (I) to all alkyl glucosides of formula (II) included in the ready-to-apply agent ranges between 1:2 and 1:10.

2. The agent according to claim 1, wherein the oxidation dye precursor of developer type (c) includes p-toluylenediamine, which is present in the form of its sulfate salt, in a quantity of 0.45 to 1.45% by weight based on the total weight of the ready-to-apply agent.

3. The agent according to claim 1, wherein the oxidation dye precursor of coupler type (d) includes one or more resorcinol derivatives selected from the group consisting of resorcinol, 2-methylresorcinol, and 4-chlororesorcinol, in a total quantity of 0.10 to 0.85% by weight, based on the total weight of the ready-to-apply agent.

4. The agent according to claim 1, wherein the oxidation dye precursor of coupler type (d) includes one or more m-aminophenol derivatives selected from the group consisting of m-aminophenol, 5-amino-2-methylphenol, and 3-amino-2-chloro-6-methylphenol, in a total quantity of 0.01 to 0.55% by weight, based on the total weight of the ready-to-apply agent.

5. The agent according to claim 1, wherein the oxidation dye precursor of type (d) includes one or more 2-aminopyridine derivatives selected from the group consisting of 3-amino-2-methylamino-6-methoxypyridine and 2-amino-3-hydroxypyridine, in a total quantity of 0.001 to 0.35% by weight, based on the total weight of the ready-to-apply.

6. The agent according to claim 1, wherein a quantity ratio of all oxidation dye precursors to all alkyl glucosides is at least 1:1 in the ready-to-apply agent.

7. The agent according to claim 1, wherein the oxidation dye precursors of coupler type (d) include resorcinol and m-aminophenol.

8. The agent according to claim 1, wherein the oxidation dye precursors of coupler type (d) include resorcinol and 3-amino-2-methylamino-6-methoxypyridine.

9. The agent according to claim 1, wherein the oxidation dye precursors of coupler type (d) include m-aminophenol and 3-amino-2-methylamino-6-methoxypyridine.

10. The agent according to claim 1, wherein the oxidation dye precursors of coupler type (d) include resorcinol, m-aminophenol, and 3-amino-2-methylamino-6-methoxypyridine.

11. The ready-to-apply agent according to claim 1, wherein the agent is produced immediately prior to application by mixing preparations (A) and (B), wherein preparation (A) is the agent of claim 1, preparation (B) is an agent which includes hydrogen peroxide in a cosmetic carrier as the oxidizing agent, and the ready-to-apply agent includes the hydrogen peroxide in a quantity of 0.5 to 8.0% by weight, calculated as 100% hydrogen peroxide, based on the total weight of the ready-to-apply agent.

12. The agent according to claim 1, further comprising an alkalizing agent selected from the group consisting of ammonia, alkanolamines, basic amino acids, and inorganic alkalizing agents such as alkaline earth or alkali metal hydroxides, alkaline earth or alkali metal metasilicates, alkaline earth or alkali metal phosphates, and alkaline earth or alkali metal hydrogen phosphates.

13. The agent according to claim 12, wherein the alkalizing agent comprises ammonia.

* * * * *